(12) United States Patent
Tsuzuki et al.

(10) Patent No.: US 7,041,505 B2
(45) Date of Patent: May 9, 2006

(54) CARRIER FOR CELL CULTURE

(75) Inventors: Hirohiko Tsuzuki, Minami-ashigara (JP); Akiko Matsuura, Minami-ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 339 days.

(21) Appl. No.: 10/384,651

(22) Filed: Mar. 11, 2003

(65) Prior Publication Data

US 2003/0228693 A1 Dec. 11, 2003

(30) Foreign Application Priority Data

Mar. 12, 2002 (JP) .............................. 2002-066376

(51) Int. Cl.
*C12N 5/00* (2006.01)
(52) U.S. Cl. ....................................... 435/401; 435/397
(58) Field of Classification Search ................ 435/177, 435/178, 180, 395, 397, 401, 402
See application file for complete search history.

(56) References Cited

U.S. PATENT DOCUMENTS 6,821,107 B1 * 11/2004 Hara et al. ................... 425/397

OTHER PUBLICATIONS

Eagle H., 1965; Proc. Exp. Biol. Med., 89: 362—cited by web page—Invitrogen.com, technical resources, media formulations.*

* cited by examiner

*Primary Examiner*—Sandra E. Saucier
*Assistant Examiner*—Satyendra K. Singh
(74) *Attorney, Agent, or Firm*—Sughrue Mion, PLLC

(57) ABSTRACT

A carrier for cell culture comprising an alginic acid gel layer laminated with a gel layer containing a cell adhesion substance, wherein the gel layer containing a cell adhesion substance has a dry thickness of less than 0.3 μm. The carrier for cell culture enables reproducible and convenient cell layer lamination without inhibiting growth and proliferation of cells upon solubilization of the carrier for preparation of a cell sheet.

11 Claims, 3 Drawing Sheets

CARRIER FOR CELL CULTURE

FIELD OF THE INVENTION

The present invention relates to a carrier for cell culture. More specifically, the present invention relates to a carrier for cell culture which can be used for cell sheet engineering.

RELATED ART

The essence of tissues constituting organs is a fabric comprising two or more kinds of cell sheets laminated by means of extracellular matrix (ECM). In the process of embryogenesis, cell sheets, which are called germ layers formed by cell-cell adhesion, cause invagination, covering, or fragmentation to develop variety of organs. Since such cell sheets are widely observed in almost all organs, techniques of combining and laminating cell sheets to reconstitute tissue structures (cell sheet engineering) have been focused (Ringai (Clinical Surgery), 56, 53–60, 2001; Materials Integration, 13, 58–64, 2000).

As techniques for laminating cell sheets, for example, a method of using N-isopropylacrylamide (NIPAM), which is a temperature responsive polymer, has been proposed. NIPAM has a property that it swells and is in a state of a liquid at a low temperature, whilst it causes phase transition at about 34° C. and rapidly shrinks to form a gel. Cells, which are cultured on NIPAM gelled under a condition of a temperature at 37° C., are laminated on another cell sheet together with NIPAM, and then the temperature is lowered to 34° C. or below to liquefy NIPAM for elimination, thereby the cells can be directly laminated (the aforementioned references as well as Shimizu T. et al., Bioscience and Bioindustry, 58, 851, 2000; Yamato M. et al., Tanpakushitsu Kakusan Koso (Protein, Nucleic acid and Enzyme), 45, 72, 2000; Yamato M. et at., Tanpakushitsu Kakusan Koso, 45, 162, 2000).

When cells are cultured on the NIPAM, the cells usually grow as a monolayer. In the culture, an ECM such as collagen is formed between adjacent cells, and for the cell growth, the cells need to adhere to the ECM. However, in the aforementioned method, upper parts of the cells and portions between the cells and the NIPAM as a base layer do not adhere to other cells, and thus the method has a problem that an ECM required for cell adhesion is not formed. Therefore, when each of the cell layer cultured on NIPAM as a monolayer is laminated and then NIPAM is eliminated by solubilization to allow the cells to directly contact with each other, the overlaid cells have insufficient anchorages for growth, and accordingly, their stable growth cannot be expected. Moreover, the liquefied NIPAM may act as a cytotoxin, and accordingly, a problem arises that a phenomenon of inhibition of normal cell growth is sometimes observed.

As a solution for the aforementioned problems, a carrier for cell culture is proposed which comprises a porous membrane laminated with an alginic acid gel layer and a gel layer comprising an extracellular matrix component or a sponge layer comprising an extracellular matrix component (Japanese Patent Unexamined Publication (Kokai) No. 2001-120267). However, this carrier for cell culture utilizes a thick extracellular matrix layer having a thickness of 0.1 to 1 mm, preferably 0.2 to 0.5 mm, and since this layer gives a dry thickness of 0.8 to 3 µm, it is impossible to store the carrier for cell culture in a dry state. Moreover, such a thick extracellular matrix layer may become an obstacle to laminating operation, which causes a problem that laminated cells cannot be reproducibly obtained. In addition, the method also has a problem that the matrix layer may become a serious obstacle to observation of laminated cells. According to the method, an aqueous solution of EDTA as a chelating agent is used for dissolution of the alginic acid gel layer to separate a cell culture from the carrier for cell culture. This operation may sometimes cause invasiveness of the cells by the chelating agent to damage the cells.

DISCLOSURE OF THE INVENTION

An object of the present invention is to provide a carrier for cell culture which can be suitably used in the field of cell sheet engineering. More specifically, the object of the present invention is to provide a means for reproducibly and easily laminating cells without inhibiting growth and proliferation of the cells upon solubilization of the carrier.

The inventors of the present invention conducted various studies to achieve the foregoing object. As a result, they found that the aforementioned problems was successfully solved by adopting a dry thickness of less than 0.3 µm for the layer containing a cell adhesion substance in the carrier for cell culture disclosed in Japanese Patent Unexamined Publication No. 2001-120267. For elimination of the alginic acid layer from a cell culture obtained by using the aforementioned carrier for cell culture, it was also found that the alginic acid layer was conveniently eliminated by a culture using a particular culture medium, and no disorder in growth or proliferation was observed in the cells obtained after the culture.

The present invention thus provides a carrier for cell culture comprising an alginic acid gel layer laminated with a gel layer containing a cell adhesion substance, wherein the gel layer containing a cell adhesion substance has a dry thickness of less than 0.3 µm.

As preferred embodiments of the present invention, there are provided the aforementioned carrier for cell culture, wherein the dry thickness of the alginic acid gel layer is from 0.1 to 10 µm; the aforementioned carrier for cell culture, wherein the gel layer containing a cell adhesion substance is formed by immersing the alginic acid gel layer in a solution containing a cell adhesion substance; the aforementioned carrier for cell culture, which comprises a porous membrane and an alginic acid gel layer formed on the porous membrane; the aforementioned carrier for cell culture, wherein the alginic acid gel is a calcium alginate gel; and the aforementioned carrier for cell culture, which is sterilized by electron beam irradiation, γ-ray irradiation, ultraviolet irradiation, or a combination thereof.

As another aspect, the present invention provides a method for cell culture, which comprises the step of culturing cells by using the aforementioned carrier for cell culture. The present invention further provides a cell culture obtained by the aforementioned culture method, wherein said cell culture has a cell layer formed on a surface of the gel layer containing a cell adhesion substance, and a cell culture obtained by subjecting the alginic acid gel layer of the aforementioned cell culture to a solubilization treatment, wherein said cell culture has a cell layer formed on a surface of the gel layer containing a cell adhesion substance. The solubilization treatment is performed by, for example, culturing the cell culture using a medium containing phosphoric acid, and preferably, the medium is substantially free from polyvalent metal cations, or contains a chelating agent in an amount of 90 mol % or more based on the total molar amount of polyvalent metal cations.

As a further aspect, the present invention provides a method for transferring and adhering the cell layer of the aforementioned cell culture to a surface of a substrate, which comprises the step of performing a culture under contact with pressure of the cell layer and the substrate; and a method for laminating the cell layer of the aforementioned cell culture on other cell layer, which comprises the step of performing culture under contact with pressure of the cell layer and the other cell layer. Preferably, the contact with pressure may be performed by weighting through a sponge. A step of solubilization treatment of the alginic acid gel layer may be performed successive to the aforementioned step. The solubilization treatment is performed by, for example, culturing the cell culture using a medium containing phosphoric acid. Preferably, the medium is substantially free from polyvalent metal cations, or contains a chelating agent in an amount of 90 mol % or more based on the total molar amount of polyvalent metal cations. The present invention further provides a cell layer adhered to a surface of substrate obtained by the aforementioned method, and laminated cell culture obtained by the aforementioned method.

PREFERRED EMBODIMENTS OF THE INVENTION

Figure 1:
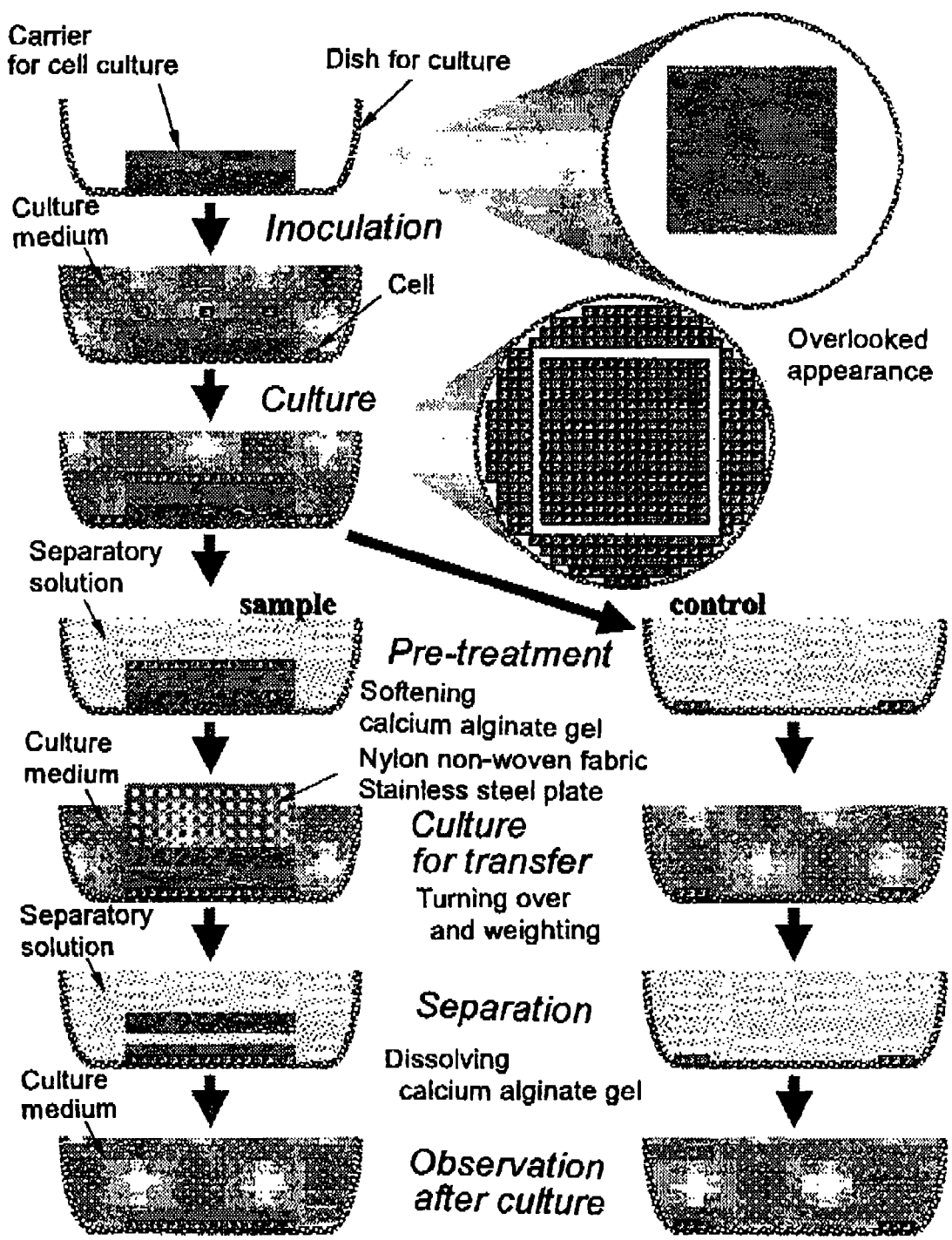
FIG. 1 depicts a procedure of cell transfer using the carrier for cell culture.

The carrier for cell culture of the present invention is a carrier for cell culture wherein an alginic acid gel layer and a gel layer containing a cell adhesion substance are laminated, and is characterized to have a dry thickness of less than 0.3 μm of the gel layer containing the cell adhesion substance. A carrier for cell culture wherein an alginic acid gel layer and an extracellular matrix substance gel layer as a cell adhesion substance gel layer are laminated on a porous membrane is disclosed in Japanese Patent Unexamined Publication No. 2001-120267. This carrier for cell culture utilizes a thick extracellular matrix layer having a thickness of 0.1 to 1 mm, preferably 0.2 to 0.5 mm, and this layer has a thickness of 0.3 to 3 μm after dryness. The carrier for cell culture of the present invention is characterized by adopting a dry thickness of less than 0.3 μm for the gel layer containing a cell adhesion substance such as an extracellular matrix, thereby the carrier for cell culture can be stored in a dried state, and laminating operation of cells can be conveniently performed to successfully obtain laminated cells with excellent reproducibility. In the specification, the "carrier for cell culture" means a structure that can be a carrier or support for culture of cells. The entire disclosure of Japanese Patent Unexamined Publication No. 2001-120267 is incorporated by reference in the disclosures of the specification.

The "alginic acid gel" means alginic acid gelled by a chelate structure formed with a carboxylic acid group in the molecule of alginic acid and a polyvalent metal ion, and "alginic acid gel layer" means alginic acid gel in the form of a layer. Alginic acid is a block copolymer consisting of glucuronic acid (G) and mannuronic acid (M), and it is considered that the polyvalent metal cation enters into a pocket structure of the M block to form an egg box and thereby cause the gelation. Specific examples of the polyvalent metal cation that can cause the gelation of alginic acid include metal ions such as barium, lead, copper, strontium, cadmium, calcium, zinc, nickel, cobalt, manganese, iron and magnesium ions. Among them, divalent metal ions are preferred, and examples include, for example, calcium ion, magnesium ion, barium ion and strontium ion. Particularly preferred is calcium ion. The "alginic acid gel" may be a polyion complex gel of alginic acid and an organic polymer compound having cationic residues. Examples of the organic polymer compound having cationic residues include compounds having two or more amino groups such as polylysine, chitosan, gelatin, and collagen.

The method of gelling alginic acid is not particularly limited, and the gelation may be achieved in a conventional manner. For example, the gelation of alginic acid can be carried out by using ion exchange. For example, when calcium ions are added to an aqueous solution of sodium alginate, ion exchange quickly occurs to give calcium alginate gel. More specifically, a calcium alginate gel layer can be obtained by adding from 0.3 to 0.5 ml (numerical ranges indicated by "(from)—to—" in the specification include lower and upper limits unless otherwise specifically referred to) of a 0.2 to 2 mass % sodium alginate aqueous solution to a cell having a bottom composed of porous membrane (e.g., membrane having a pore size of 3.0 microns produced by FALCON), then allowing a 0.01 to 0.1 M calcium chloride aqueous solution to infiltrate from the porous membrane, and leaving the system at 20 to 30° C. for 0.5 to 1 hour. By the gelation of alginic acid using the porous membrane as described above, a carrier for cell culture can be obtained which comprises the porous membrane and an alginic acid gel layer laminated on the porous membrane. However, the use of the porous membrane for the gelation of alginic acid is not essential for the carrier for cell culture of the present invention, and the carrier for cell culture of the present invention may be produced by using a separately prepared alginic acid gel.

According to the present invention, the dry thickness of the alginic acid gel layer is not particularly limited. For example, the thickness is preferably from 0.1 to 10 μm, more preferably from 0.5 to 5 μm In the specification, the dry thickness of the gel layer means generally a thickness of a gel layer measured under a sufficiently dried condition, for example, under a condition wherein moisture contained in a gel is less than 100 mass % based on the total weight of the gel. When a solid content of the alginic acid gel layer is too small, a satisfactory gel membrane may not be formed, which sometimes results in formation of holes. When a solid content of the alginic acid gel layer is too large, problems may sometimes arise in that curling or cracks may be formed in a gel membrane during drying process, or deformation during culture step and poor dissolution in alginic acid gel dissolution step may be caused. The thickness of the alginic acid gel layer can be measured by using an electron microscopic cross-sectional image, thickness gage, ellipsomter, variable angle XPS or the like, and a value measured from an electron microscopic cross-sectional image is preferably used.

Alginic acid exists in nature as a cell wall-constituting polysaccharide or intercellular filling substance of brown algae, and can be obtained from the algae as raw materials. Examples of the brown algae as a raw material include brown algae belonging to Order Fucales, Family Durvilleaceae, Genus *Durvillea* (e.g., *D. potatorum*), Order Fucales, Family Fucaceae, Genus *Ascophyllum* (e.g., *A. nodosum*), Order Laminariales, Family Laminariaceae, Genus *Laminaria* (e.g., *Laminaria japonica, Laminaria longissima*), Order Laminariales, Family Laminariaceae, Genus *Eisenia* (e.g., *Eisenia bicyclis*), Order Laminariales, Family Laminariaceae, Genus *Ecklonia* (e.g., *Ecklonia cava, Ecklonia kurome*), and Order Laminariales, Family Lessoniaceae, Genus *Lessonia* (e.g., *L. flavikans*). Commercially available alginic acid can also be used. A G/M ratio of alginic acid is not particularly limited. A larger G/M ratio provides a higher gel formation ability, and accordingly, a larger G/M ratio is more preferred. Specifically, the ratio may preferably be from 0.1 to 1, more preferably from 0.2 to 0.5.

The gel layer containing a cell adhesion substance means hydrogel in the form of a layer containing a substance having a cell adhesion property. The type of the cell adhesion substance is not particularly limited, and any substances may be used so long as they do not have cytotoxicity and can form a gel to which cells adhere under an ordinary culture condition. The cell adhesion substance may be either of a natural or a non-natural compound. The substance may preferably be an extracellular matrix component. The extracellular matrix is generally defined as "a stable biological structure existing extracellularly in an animal tissue and a complex aggregate formed by biological polymers which are synthesized by cells, and secreted and accumulated outside the cells" (Dictionary of Biochemistry (3rd edition), p. 570, Tokyo Kagaku Dojin), and the matrix plays roles of physically supporting cells, regulating cellular activities (i.e., a role of transmitting extracellular information to a cell to change its activities) and the like. The "extracellular matrix component" means a constituting ingredient of the extracellular matrix. Specific examples include collagen, elastin, proteoglycan, glucosaminoglycan (hyaluronic acid, choadroitin sulfate, dermatan sulfate, heparan sulfate, heparin, keratan sulfate and the like), fibronectin, laminin, vitronectin and the like.

Preferred examples of the cell adhesion substance used for the manufacture of the carrier for cell culture of the present invention include, for example, collagen, atelocollagen, Matrigel (gel consisting of type IV collagen, laminin and heparan sulfate) and hyaluronic acid. The extracellular matrix component can be obtained in a conventional manner, and commercially available extracellular matrix components may also be used. The cell adhesion substance can be gelled in a conventional manner. For example, when the cell adhesion substance is collagen, a collagen gel can be obtained by incubating a 0.3 to 0.5% aqueous solution of collagen at 37° C. for from 10 to 20 minutes. A gelling agent may be used for the gelation of the extracellular matrix component, if needed.

The dry thickness of the cell adhesion gel layer in the carrier for cell culture of the present invention is less than 0.3 µm. The lowest limit of the thickness is not particularly limited. The lowest limit may usually be 0.005 µm. The thickness is preferably from 0.005 to 0.2 µm. The thickness of the cell adhesion gel layer can be measured by using an electron microscopic cross-sectional image, thickness gage, ellipsomter, variable angle XPS or the like, and can be preferably measured from an electron microscopic cross-sectional image.

The method for laminating the cell adhesion substance gel layer on the alginic acid gel layer is not particularly limited. The term "laminated" used in the specification means a state wherein two or more layers are laminated. The alginic acid gel layer may consist of two or more layers, and/or the cell adhesion gel layer may consist of two or more layers. An example of the method of laminating the layers include, for example, a method of separately preparing the alginic acid gel layer and the cell adhesion substance gel layer and then laminating the two layers. Preferred is a method of laminating an aqueous solution containing a cell adhesion substance on an alginic acid gel layer and then gelling the aqueous solution. Further, for laminating the alginic acid gel layer and the cell adhesion gel layer of the carrier for cell culture of the present invention, a method of immersing the alginic acid gel layer in a solution of a cell adhesion substance can be preferably used. By applying this method, a gel of the cell adhesion substance having a dry thickness of less than 0.3 µm can be conveniently and reliably laminated on an alginic acid gel layer. For example, a method can be exemplified in which a calcium alginate gel layer prepared by the aforementioned method is immersed in a commercially available 0.3 to 0.5 mass % collagen aqueous solution, washed with water, and then dried. The gel layer of the cell adhesion substance may be coated on the alginic acid gel layer by using appropriate means.

According to a preferred embodiment of the carrier for cell culture of the present invention, for example, the alginic acid gel layer can be formed on a porous membrane, and the cell adhesion gel layer can be laminated on the alginic acid gel layer. The type of the porous membrane is not particularly limited, and any membrane may be used so long as it does not allow passage the alginic acid gel but allows passage of metal ions and the like. As the porous membrane, a membrane having small pores, as well as a membrane having voids and that having both of small pores and voids or the like may be used. Specific examples of the porous membrane include, for example, filter paper, ultrafiltration membranes, silicone rubber membranes, tetrafluoroethylene resin porous membranes (PTPE porous membranes), non-woven fabric, gauze-like mesh, various membrane filters (nylon, polyvinylidene fluoride, acetylcellulose, cellulose nitrate, polyethylene terephthalate, polycarbonate and the like), and preferred are membrane filters, in particular, membranes of nylon membrane filters. When the porous membrane has small pores, the sizes of pores are usually from 0.02 to 1,000 µm, preferably from 0.02 to 100 µm, more preferably from 0.1 to 10 µm.

The carrier for cell culture of the present invention is useful for the manufacture of a cell sheet. Types of cells that can be cultured are not particularly limited. Examples thereof include, for example, fibrocytes, vascular endothelial cells, chondrocytes, hepatocyted, small intestine epithelial cells, epidermal keratinocytes, osteoblasts, bone marrow mesenchymal cells and the like, and preferred examples include fibrocytes. For the cell culture, a culture medium (for example, D-MEM medium, MEM medium, HamF12 medium, or HamF10 medium) having a cell density of from 10,000 to 15,000 cells/ml can usually be added onto the cell adhesion gel layer. The cell culture conditions are not particularly limited and appropriately chosen by those skilled in the art depending on the type of cells to be cultured. In general, when cells are cultured on the cell adhesion gel layer, the culture may preferably be continued until a confluent cell monolayer is formed on the cell adhesion gel layer.

Culture of cells using the carrier for cell culture of the present invention can be performed specifically as follows. The carrier for cell culture is placed inside a petri dish or the like, then an appropriate culture medium (for example, D-MEM medium, MEM medium, HamF12 medium, HamP10 medium) is added to the petri dish to immerse the carrier for 5 minutes, and then the medium is exchanged. After this procedure is repeated three times, the culture system was left for 12 to 24 hours so that the culture medium can infiltrate into the carrier for cell culture. Then, the culture medium in the petri dish is discarded, and then cells are inoculated onto the cell adhesion gel layer of the carrier for cell culture, and further an appropriate culture medium (for example, D-MEM medium, MEM medium, HamF12 medium, HamF10 medium) is added to the petri dish. After the system is left at 37° C. for 1 to 2 hours so that the cells can be held by (adhered to) the cell adhesion gel layer, the culture is continued at 37° C. During the culture, the culture medium may be exchanged, if needed. Usually, the culture medium is exchanged every 0.5 to 2 days of the culture.

A cell culture obtained by culturing cells using the carrier for cell culture of the present invention contains the carrier for cell culture of the present invention and a cell layer formed on the cell adhesion gel layer of the carrier for cell culture. A cell culture according to another embodiment can be obtained from the aforementioned cell culture by subjecting the alginic acid gel layer to a solubilization treatment, and generally can be obtained in the form of a cell sheet.

The method for the solubilization treatment applied to the alginic acid gel layer is not particularly limited. The treatment can be preferably carried out by removing cation components that constitute the alginic acid gel. When the cation species is a polyvalent metal cation, the treatment can be performed by reduction of the polyvalent metal cations using addition of ions that form a complex or hardly soluble salt with the polyvalent metal cation, such as phosphate, or concealment of the polyvalent metal cations using addition of a chelating agent or the like. Preferably, the alginic acid gel layer can be conveniently and efficiently solubilized by culturing the aforementioned cell culture using a medium containing phosphoric acid. The medium is preferably a medium free from polyvalent metal cations. When the polyvalent metal cations are contained, it is desirable to form a chelate of polyvalent metal cations in an amount of 90 mol % or more based on the total molar number of the polyvalent metal cations by using a chelating agent. For the chelate formation, a concentration of the chelating agent may preferably be from 90 to 10,000 mol % or less, more preferably 90 to 1,000 mol %, based on the total molar amount of the polyvalent metal cations.

The type of the chelating agent is not particularly limited. Examples include, for example, ethylenediamine-di-ortho-hydroxyphenylacetic acid, diaminopropanetetraacetic acid, nitrilotriacetic acid, hydroxyethylethylenediaminetriacetic acid, dihydroxyethylglycine, ethylenediaminediacetic acid, ethylenediaminedipropionic acid, iminodiacetic acid, diethylenetriamiaepeataacetic acid, hydroxyethyliminodiacetic acid, 1,3-diaminopropanoltetraacetic acid, triethylenetetraminehexaacetic acid, trans-cyclohexanediaminetetraacetic acid, ethylenediaminetetraacetic acid (EDTA), glycol ether-diaminetetraacetic acid, O,O'-bis(2-aminoethyl)ethylene glycol-N,N,N',N'-tetraacetic acid (EGTA), ethylenediamine-tetrakismethylenephosphonic acid, diethylenetriaminepentamethylenephosphonic acid, nitrilotrimethylenephosphonic acid, 1-hydromyethylidene-1,1-diphosphonic acid, 1,1-diphosphonoethane-2-carboxylic acid, 2-phosphonobutane-1,2,4-tricarboxylic acid, 1-hydroxy-1-phosphonopropane-1,3,3-tricarboxylic acid, catechol-3,5-disulfonic acid, sodium pyrophosphate, sodium tetrapolyphosphate and sodium hexametaphosphate. Preferred examples are diethylenetri-aminepentaacetic acid, triethylenetetraminehexaacetic acid, 1,3-diaminopropanoltetraacetic acid, glycol ether-diaminetetraacetic acid, hydroxyethylethylenediaminetriacetic acid, 2-phosphonobutane-1,2,4-tricarboxylic acid, 1,1-diphosphonoethane-2-carboxylic acid, nitrilotrimethylenephosphonic acid, ethylenediaminetetraphosphonic acid, diethylenetriaminepentaphosphonic acid, 1-hydroxypropylidene-1,1-diphosphonic acid, 1-aminoethylidene-1,1-diphosphonic acid, 1-hydroxyethylidene-1,1-diphosphonic acids and salts thereof. Among them, particularly preferred are EDTA and EGTA.

When the alginic acid gel layer is formed on a porous membrane, the solubilization treatment of the alginic acid gel layer using a chelating agent is preferably carried out by infiltrating a chelating agent from the porous membrane. By such operation, the porous membrane and the alginic acid gel layer can be easily separated, and the cell culture can be easily removed from the porous membrane. It is not necessary to completely remove the alginic acid gel layer by the solubilization treatment of the alginic acid gel layer, and the alginic acid gel layer remain unsolubilized may be left on the cell culture. However, the alginic acid gel layer is preferably solubilized as much as possible and removed.

The cell culture obtained by subjecting the alginic acid gel layer to the solubilization treatment contains a cell layer (cell sheet), and accordingly, the cell culture can be used for lamination or transfer and adhesion of cell layers, For lamination of cell layers, the cell layer of the cell culture obtained as described above can be cultured under contact with pressure to other cell layer. As the other cell layer, a cell layer formed on the carrier for cell culture of the present invention may be used. Kinds of cells of the cell layers to be laminated may be the same or different. The number of the cell layers to be laminated is not particularly limited. Generally the number is from 1 to 10, preferably from 1 to 5, more preferably from 1 to 3. Transfer and adhesion of a cell layer can be achieved by culturing the cell layer of the cell culture obtained as described above under contact with pressure to other substrate for cell culture. For the lamination or the transfer and adhesion of cell layers, the alginic acid gel may be solubilized, as required. A preferred method for the lamination or the transfer and adhesion comprises the step of carrying out culture with weighting on the cells cultured beforehand or on the other substrate for cell culture, and then dissolving the alginic acid gel.

The contact with pressure between cell layers or between a cell layer and a substrate may be performed by any method. A preferable state of contact with pressure can be obtained by applying weight from the side of the alginic acid gel of the carrier for cell culture of the present invention (when the alginic acid gel is formed on a porous membrane, from the bottom side of the porous membrane). If cells are sealed by weighting, cells may sometimes be smothered. Therefore, the substrate for receiving the transfer or a cell culture substrate on which a cell layer to be laminated is formed may preferably consist of a wafer-permeable gel, porous membrane, or a combination thereof. Further, for uniform transfer and adhesion of a cell layer, a weight should be applied so as to sufficiently cover the surface of the cell layer. However, uniform contact may disturb diffusion of oxygen, and therefore, a weight may preferably be applied through non-fabric sheet (nylon, polyester, stainless steel and the like) or the like so as not to be a barrier to diffusion of oxygen. The weight to be applied may be, for example, preferably from about 0.1 to 50 $g/cm^2$, more preferably from about 0.50 to 10 $g/cm^2$. The culture time of the cells under weighing is not particularly limited, and can be appropriately chosen so that sufficient transfer and adhesion or lamination of cells can be achieved. Generally, the period of time may be 4 to 72 hours, preferably from 6 to 48 hours.

When a preparation solution containing a carbodiimide is used for the preparation of the carrier for cell culture of the present invention, adhesion of cells may sometimes be improved. Carbodiimides and N-hydroxysuccinimide may be added to a preparation solution for any layer. The agents may preferably be added to a preparation solution for the alginic acid layer or impregnated into a porous membrane beforehand. Alternatively, it is also preferred to immerse the carrier, after application of the alginic acid layer, in a solution in which the agents are dissolved together with calcium chloride. The carbodiimides are preferably water-soluble. Examples include, for example, 1-ethyl-3-(3-dimethylaminopropyl)carbodiimide hydrochloride and the like. A concentration of the carbodiimide is not particularly limited, and can be appropriately chosen depending on the type of the cells and the like. For example, the concentration may preferably be from 0.1 to 200 g/L, more preferably from 1 to 100 g/ml. For the use of the carbodiimides, N-hydrozysuccinimide may be used as a catalyst, and its concentration may preferably be from 1 to 50 weight % based on the carbodiimide.

The carrier for cell culture of the present invention may be sterilized by any method. Sterilization by radiation such as electron beam, γ-ray, X-ray, and ultraviolet ray may preferably be used. An electron beam, γ-ray, and ultraviolet ray are more preferably used, and electron beam sterilization is particularly preferred. An exposure dose for the electron beam sterilization is not particularly limited and suitably chosen by those skilled in the art. The dose may preferably be from 0.1 to 65 kGy, most preferably from 1 to 40 kGy. Chemical sterilization such as ethylene oxide gas sterilization and sterilization using a high temperature such as high pressure steamy gas sterilization may be sometimes not preferred, because the cell adhesion layer and the alginic acid gel layer may be decomposed. The aforementioned sterilization methods may be used alone or in combination. The same sterilization may be repeated. A carrier for cell culture sterilized as described above can be stored at room temperature for a long period of time, if it is stored under a sterile condition. The carrier for cell culture of the present invention may also be provided in a dried state.

By using vascular endothelial cell layers or hepatocyte layers as the laminated cell layers provided by the present invention, for example, a three-dimensional tissue structure of the liver can be constructed. The three-dimensional tissue structure can be used for, for example, in vitro permeability tests of drugs, and can also be utilized as a substitute model for an animal experiment or as an organ for transplantation. The laminated cell layers can be cultured under a culture condition suitable for the type of cells constituting the cell layer. For the culture, for example, D-MEM medium, MEM medium, HamF12 medium, HamF10 medium and the like can be used as the medium.

EXAMPLES

The present invention will be more specifically explained by referring to the following examples. However the scope of the present invention is not limited to these examples.

Example 1

Preparation of Carrier for Cell Culture (1) Preparation of Nylon Microfilter 13.7 g of 6-nylon was dissolved in 66.3 g of formic acid, left overnight, added with 20 ml of water and dispersed by using a homogenizer to obtain a nylon dope. The obtained nylon dope was applied on a stainless steel substrate with a thickness of 250 $ml/m^2$, and the coated substrate was immersed in a 45 weight % aqueous solution of formic acid.

After the coated layer became sufficiently cloudy, the coated substrate was washed with running water to obtain a nylon microfilter. The nylon microfilter was stored in water without dryness.

(2) Formation of Calcium Alginate Layer (i) Preparation of Simple Calcium Alginate Membrane with Glass Substrate An aqueous solution containing 1 weight % of sodium arginate (produced by Wako Pure Chemical Industries), 3.2 weight % of 1-ethyl-3-(3-dimethylaminopropyl)carbodiimide hydrochloride (WSC, produced by Peptide Institute), 0.34 weight % of N-hydroxysuccinimide (NHS, produced by Peptide Institute) and 0.3 weight % of lysine (produced by Wako Pure Chemical Industries) was applied on a glass substrate with a thickness of 670 ml/m$^2$ and left standing at 40° C. for 3 hours to cause gelation of the solution Then, the substrate was immersed in a 0.1 M aqueous solution of calcium chloride for 1 hour and washed with running water to obtain a simple calcium alginate membrane with a glass substrate. The thickness of the dry alginic acid gel layer was 5 μm as measured by using a thickness gage.

(ii) Preparation of Nylon Microfilter/Calcium Alginate Laminate Membrane

Moisture on the nylon microfilter obtained in (1) was wiped with paper, the filter was immersed in a 0.1 M aqueous solution of calcium chloride, and a 1 weight % aqueous solution of sodium alginate was applied on the filter with a thickness of 100 ml/m$^2$. The coated substrate was immersed in an aqueous solution containing 0.1 M calcium chloride and 10 mg/l of WSC and washed with running water to obtain a nylon microfilter/calcium alginate laminate membrane. The thickness of the alginic acid gel layer dry membrane was 0.75 μm as measured from an electron microscopic cross-sectional image.

Figure 2:
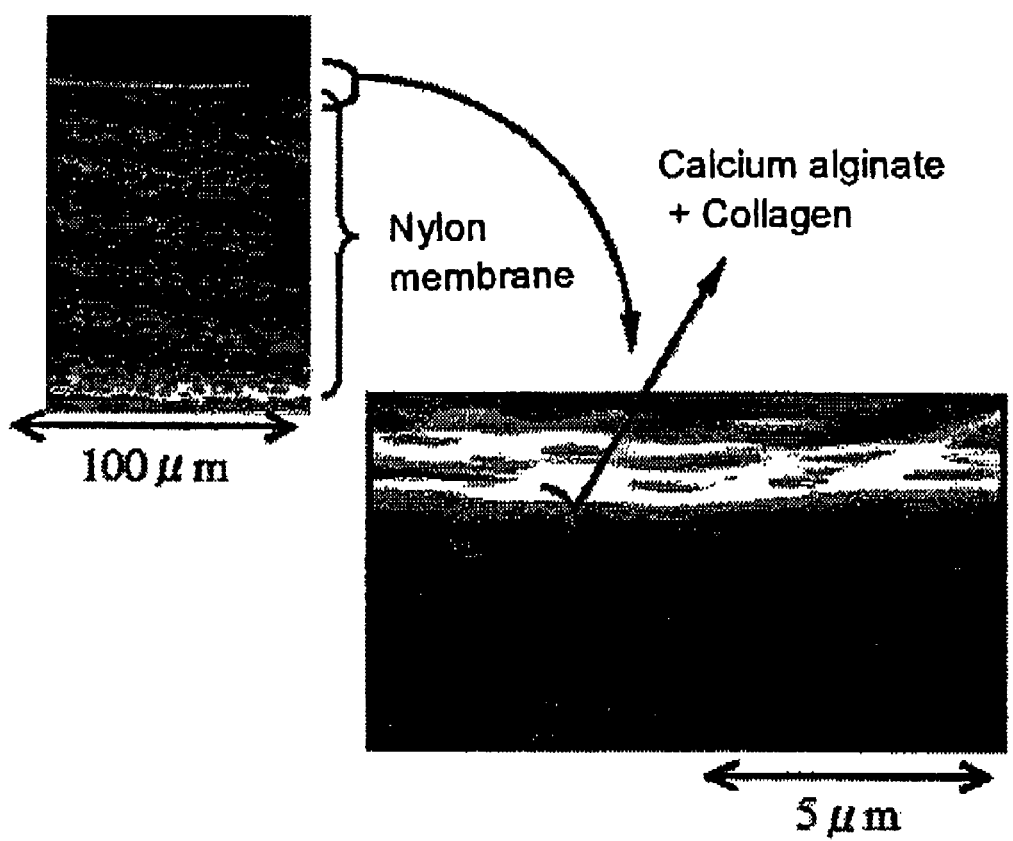
FIG. 2 shows electron microscopic cross-sectional images of cell culture using the carrier for cell culture.

(3) Modification with Collagen Layer (i) Modification with Extremely Thin Collagen Layer Each of the simple calcium alginate membrane with glass substrate and the nylon microfilter/calcium alginate laminate membrane in a non-dried state obtained in (2) was immersed in a 10-fold aqueous dilution of Cellmatrix I-C (produced by Nitta Gelatin), washed with running water and dried to obtain membranes modified with an extremely thin collagen layer (Ia: membrane with glass substrate, Ib: membrane with microfilter). The total thickness of the collagen layer and the alginic acid gel layer was determined to be 0.8 μm from an electron micrograph, and the thickness of the collagen layer was calculated to be 0.05 μm as a difference of the total thickness and the alginic acid gel layer thickness of 0.75 μm (see, FIG. 2). Further, another nylon microfilter/calcium alginate laminate membrane was prepared by coating sodium alginate with a larger thickness of 20 μm and providing the same collagen layer as that of Ib, and designated as IV.

(2) Coating of Thin Collagen Layer

In a volume of 10 ml of Cellmatrix I-P (produced by Nitta Gelatin) was added with 80 ml of distilled water and 10 ml of 10× Dulbecco's phosphate buffered saline (pH 7.1, produced by GIRCO) with cooling with ice water to obtain a solution before gelation. The solution before gelation was coated on the extremely thin collagen layer-modified membranes obtained in (i) and gelled at 40° C. Then, the coated membranes were washed with running water and dried to obtain thin collagen layer-coated alginic acid gel membranes (IIa: membrane with glass substrate, IIb: membrane with microfilter). The total thickness of the collagen layer was found to be 0.3 μm as measured from an electron microscopic image.

(4) Comparative Example

In the preparation of membrane IIb, the coating was performed so as to give a dry thickness of 1 μm of a collagen layer to obtain membrane III. The resulting product was found to be unsuitable as a carrier for cell culture, because cracks were generated during drying.

Example 2

Sterilization

When the membrane Ib obtained in Example 1 was subjected to each of six different sterilizations, i.e., UV sterilization for 1, 2 and 3 hours and electron beam sterilization at 20, 40, 60, 80 and 100 kGy, no bacterium was found in each of the samples. In the samples not subjected to any sterilization treatment, 5900 cells/m$^2$ of bacteria were found. However, the samples subjected to electron beam sterilization at 60, 80 or 100 kGy were found to be discolored, and any of the layers constituting the membranes was possibly denatured. The discoloration was remarkable in the samples subjected to electron beam sterilization at 80 or 100 kGy.

Example 3

Cell culture Utilizing Carrier for Cell Culture

Cells were cultured by using the carrier for cell cultures as follows.

(1) Used Cell

CHL (Chinese Hamster Lung Cell)

(2) Used Medium

Eagle's minimum medium containing 10% bovine fetal serum (3) Carrier for Cell Culture The carrier for cell cultures prepared in Example 1, adhered to bottom surfaces of polystyrene cell culture dishes with double-sided tapes, and a polystyrene cell culture alone as a comparative example were subjected to UV sterilization or electron beam sterilization. The operation, wherein the medium was added to the dishes to immerse the carrier for cell cultures for 5 minutes and then the medium was exchanged, was repeated three times, and then the dishes were left overnight to allow the medium to infiltrate into the carrier for cell cultures. The combinations of the used carrier for cell cultures and sterilization methods are shown in Table 1.

(4) Inoculation of Cells

The cells cultured beforehand were collected by trypsin treatment, and the cell density was adjusted to 50,000 cells/ml. After the medium in the cells and dishes was discarded, the cell suspension was inoculated into the dishes at a cell number of 10,000 cells/cm², and then the medium was added.

(5) Culture

The cells were cultured at 37° C. for two days by using a $CO_2$ incubator.

(6) Results

No problem was observed for each of the samples with respect to cell adhesion, separation of carrier for cell culture, and toxicity.

Example 4

Separation of Cell Layer

The samples obtained by the culture in Example 3 were immersed in each of the following seven kinds of separatory solutions and non-separatory solutions, and then the cell layers were pulled with a pair of tweezers to examine state of separation of the cell layers from the carrier for cell cultures. A period of time required for the separation of each cell layer was measured. Then, each separated cell sheet was placed on a polystyrene cell culture dish, added with the medium and cultured at 37° C. for one day by using a $CO_2$ incubator. The cells were stained with trypan blue and observed under an optical microscope. The results are shown in Table 1. The membranes according to the present invention gave favorable separatory property.

(1) Separatory Solution
 (i) Distilled water
 (ii) 0.01 M EDTA aqueous solution
 (iii) 10× Dulbecco's phosphate buffered saline diluted 10 times with distilled water
 (iv) Eagle's minimum medium in which calcium ions and magnesium ions were replaced with potassium ions
 (v) Eagle's minimum medium added with EDTA in an amount of 100 mol % with respect to the total molar amount of calcium ions and magnesium ions (2) Non-Separatory Solution
 (vi) In a volume of 0.1 ml of a solution obtained by dissolving 4.0 g of anhydrous calcium chloride and 4.0 g of magnesium chloride hexahydrate in 40 ml of distilled water was added to 100 ml of the solution of (iii).
 (vii) Eagle's minimum medium

TABLE 1

| Sample | Cell culture carrier | Sterilization | Separatory solution (separatory time/survival rate of cells/degree of ease of observation) | | | | | Non-separatory solution | | |
|---|---|---|---|---|---|---|---|---|---|---|
| | | | (i) | (ii) | (iii) | (iv) | (v) | (vi) | (vii) | |
| 1 | Ia | UV 3 h | 25 min/X/◯ | 15 min/X/◯ | 20 min/Δ$^X$/◯ | 20 min/◯$^Δ$/◉ | 20 min/◯$^Δ$◉ | Not separated | Not separated | Invention |
| 2 | Ib | UV 1 h | 20 min/X/◉ | 10 min/X/◉ | 15 min/Δ/◉ | 15 min/◉/◉ | 15 min/◉/◉ | Not separated | Not separated | Invention |
| 3 | Ib | UV 2 h | 20 min/X/◉ | 10 min/X/◉ | 15 min/Δ/◯ | 15 min/◉/◉ | 15 min/◉/◉ | Not separated | Not separated | Invention |
| 4 | Ib | UV 3 h | 20 min/X/◉ | 10 min/X/◉ | 15 min/Δ/◯ | 15 min/◉/◉ | 15 min/◉/◉ | Not separated | Not separated | Invention |
| 5 | Ib | Electron beam 20 kGy | 15 min/X/◉ | 10 min/X/◉ | 10 min/Δ/◯ | 10 min/◉/◉ | 10 min/◉/◉ | Not separated | Not separated | Invention |
| 6 | Ib | Electron beam 40 KGy | 15 min/X/◉ | 10 min/X/◉ | 10 min/Δ/◯ | 10 min/◉/◉ | 10 min/◉/◉ | Not separated | Not separated | Invention |
| 7 | Ib | Electron beam 60 kGy | 15 min/X/◉ | 10 min/X/◉ | 10 min/Δ/◯ | 10 min/◉/◉ | 10 min/◉/◉ | Not separated | Not separated | Invention |
| 8 | Ib | Electron beam 80 kGy | 15 min/X/◉ | 10 min/X/◉ | 10 min/Δ◯ | 10 min/◉/◉ | 10 min/◉/◉ | Not separated | Not separated | Invention |
| 9 | Ib | Electron beam 100 kGy | 15 min/X/◉ | 10 min/X/◉ | 10 min/Δ/◯ | 10 min/◉/◉ | 10 min/◉/◉ | Not separated | Not separated | Invention |
| 10 | IIa | UV 3 h | 30 min/X/Δ | 20 min/X/Δ | 25 min/Δ$^X$/Δ | 20 min/◯$^Δ$/Δ | 25 min/◯$^{ΔΔ}$ | Not separated | Not separated | Invention |
| 11 | IIb | UV 3 h | 25 min/X/Δ | 20 min/X/Δ | 20 min/Δ$^X$/Δ | 20 min/◯/Δ | 20 min/◯/Δ | Not separated | Not separated | Invention |
| 12 | III | UV 3 h | 90 min/X/X | 60 min/X/X | 30 min/X/X | 40 min/Δ$^X$/X | 40 min/Δ$^X$/X | Partially separated | Partially separated | Comparative |
| 13 | IV | UV 3 h | 30 min/Δ$^X$/◯ Comparative | 20 min/X/◯ Comparative | 30 min/Δ$^X$/◯ Comparative | 30 min/Δ◯ Invention | 30 min/Δ/◯ Invention | Not separated | Not separated | Invention |

<Evaluation criteria for cell survival rate>
◉: 90% or more of cells are alive.
◯: 70% or more of cells are alive.
◯$^Δ$: 50% or more of cells are alive.
Δ: 30% or more of cells are alive.
Δ$^X$: 10% or more of cells are alive.
X: Alive cells are 10% or less.

<Evaluation criteria for cell observation>
◉: Detailed states inside of a cell can be clearly observed.
◯: States of a cell can be sufficiently observed.
Δ: Detailed states inside a cell is unclear.
X: Outline of a cell can be observed with much difficulty.

Example 5

Transfer of a Cell Layer

The samples obtained by the culture on the carrier for cell cultures Ib, IIb, III and IV in Example 3 (Samples 2 to 9 and 11 to 13 mentioned in Table 1) were taken out together with the carrier for cell cultures, and placed on polystyrene cell culture dishes in a manner that the cell layer surfaces were contacted with the dishes, and then nylon non-woven fabric (Scotch Bright produced by 3M) and stainless steel plates were placed thereon. The weight of each stainless steel plate was adjusted so that the total weight including the weight of the nylon non-woven fabric became 0.8 g/cm². Then, the samples were immersed in the separatory solution (iv) or (v) in Example 4 for 10 minutes, and after the solution was replaced with the medium, incubation was continued at 37° C. for one day by using a $CO_2$ incubator. The samples incubated as described above were immersed in a separatory solution for 20 minutes, and then the carrier for cell cultures were separated by pulling with a pair of tweezers. Then, the solution was replaced with the medium, and culture was continued at 37° C. for one day by using a $CO_2$ incubator. The cells were stained with trypan blue and then observed under an optical microscope. The results are shown in Table 2. Favorable results were obtained for the samples of the present invention. In the samples where the weight was applied only by using the stainless steel plates without the nylon non-woven fabric and the samples where the separatory solution (i), (ii) or (iii) was used, the cells died during the transfer operation. Further, in the samples where the separatory solution (vi) or (vii) was used, transfer was not successful.

TABLE 2

| Sample | Cell culture carrier | Sterilization | Transfer (iv) | (v) | |
|---|---|---|---|---|---|
| 2 | Ib | UV 1 h | ◎ | ◎ | Invention |
| 3 | Ib | UV 2 h | ◎ | ◎ | Invention |
| 4 | Ib | UV 3 h | ◎ | ◎ | Invention |
| 5 | Ib | Electron beam 20 kGy | ◎ | ◎ | Invention |
| 6 | Ib | Electron beam 40 kGy | ◎ | ◎ | Invention |
| 7 | Ib | Electron beam 60 kGy | ◎ | ◎ | Invention |
| 8 | Ib | Electron beam 80 kGy | ◎ | ◎ | Invention |
| 9 | Ib | Electron beam 100 kGy | ◎ | ◎ | Invention |
| 11 | IIb | UV 3 h | ○*2 | ○*2 | Invention |
| 12 | III | UV 3 h | X | X | Comparative |
| 13 | IV | UV 3 h | Δ | Δ | Invention |

<Evaluation criteria for ease of cell observation>
◎: 95% or more of cells are alive. 95% or more of cells are uniformly transferred.
○: *1 95% or more of cells are alive. About 70% of cells are transferred, but there are portions not transferred.
*2 95% or more of cells are alive. 95% or more of cells are uniformly transferred, but detailed states inside cells are unlcear because no sharp optical microscopic image can be obtained.
Δ: About 70% of cells are alive. About 50% of cells are transferred, but there are portions not transferred. Further, detailed states inside cells are unclear because no sharp optical microscopic image can be obtained.
X: Alive cells are 50% or less. Transferred cells are 10% or less. Further, detailed states inside cells are unclear because no sharp light microscopic image can be obtained.

Example 6

Lamination of cell layers

By using the carrier for cell culture Ib in Example 1 subjected to UV sterilization for 2 hours as in Example 2 and a polystyrene cell culture dish, the following cells were cultured in the same manner as in Example 3.
CHL (Chinese Hamster Lung Cell)
BRL (Buffalo Rat Liver 3A, ATCC No.: CRL 1442)
BAE (Bovine Aortic Endothelial Cell)

Figure 3:
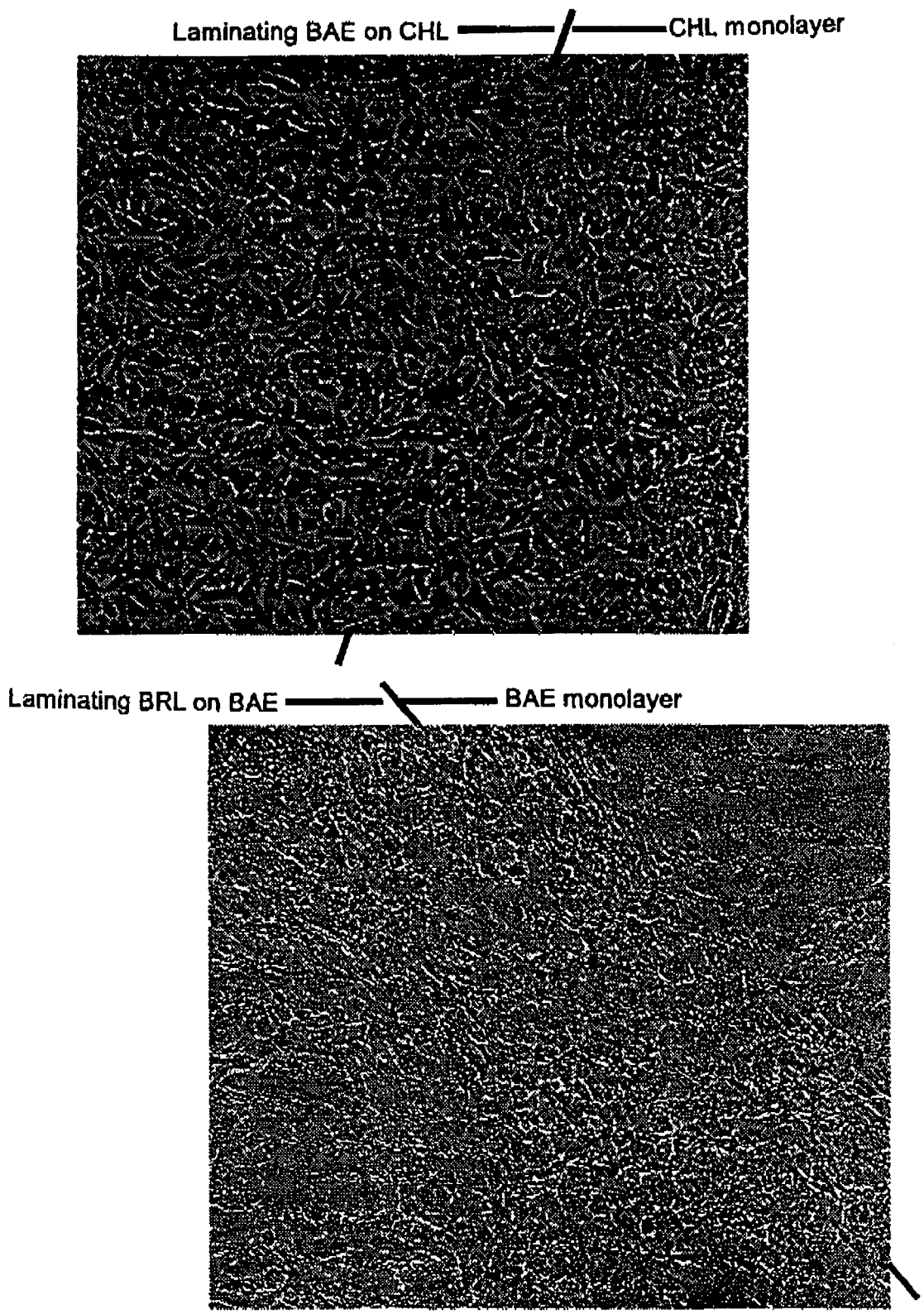
FIG. 3 shows optical microscopic photographs of cells laminated by using the carrier for cell culture of the present invention.

On each of the three types of cells cultured on dishes as described above, each of three types of cells was cell-transferred in the same manner as in Example 5 by using the separatory solution (v) in Example 4 to obtain nine types in total of laminated cells. Each of the laminated cells was cultured in the medium for 90 hours and then stained with trypan blue, and the state of the cells was observed under an optical microscope. As a result, it was found that each of the laminated cells were favorably cultured. BAE laminated on CHL and BRL laminated on BAE are shown in FIG. 3 for examples.

It is clearly understood from the above experimental results that the carrier for cell culture of the present invention facilitates lamination of cell layers.

What is claimed is:

1. A carrier for cell culture comprising an alginic acid gel layer laminated with a gel layer containing a cell adhesion substance, wherein the gel layer containing a cell adhesion substance has a dry thickness of from 0.005 μm to 0.2 μm.

2. The carrier for cell culture according to claim 1, wherein the dry thickness of the alginic acid gel layer is from 0.1 to 10 μm.

3. The carrier for cell culture according to claim 1, wherein the gel layer containing a cell adhesion substance is formed by immersing the alginic acid gel layer in a solution containing a cell adhesion substance.

4. The carrier for cell culture according to claim 1, which comprises a porous membrane and an alginic acid gel layer formed on the porous membrane.

5. The carrier for cell culture according to claim 1, wherein the alginic acid gel is a calcium alginate gel.

6. A method for cell culture, which comprises the step of culturing cells by using the carrier for cell culture according to claim 1.

7. A cell culture obtained by the method according to claim 6, wherein said cell culture has a cell layer formed on a surface of the gel layer containing a cell adhesion substance.

8. A method for transferring and adhering a cell layer of the cell culture according to claim 7 to a surface of a substrate, which comprises the step of performing a culture under contact with pressure of the cell layer and the substrate.

9. The method according to claim 8, which further comprises the step of solubilization treatment of the alginic acid gel layer.

10. A method for laminating a cell layer of the cell culture according to claim 7 on other cell layer, which comprises the step of performing culture under contact with pressure of the cell layer of said cell culture and the other cell layer.

11. The method according to claim 10, which further comprises the step of solubilization treatment of the alginic acid gel layer.

* * * * *